United States Patent [19]

McGredy, IV

[11] Plant 4,503

[45] Feb. 19, 1980

[54] ROSE PLANT

[75] Inventor: Samuel McGredy, IV, Auckland, New Zealand

[73] Assignee: Armstrong Nurseries, Inc., Ontario, Calif.

[21] Appl. No.: 969,800

[22] Filed: Dec. 15, 1978

[51] Int. Cl.[2] ..... A01H 5/00

[52] U.S. Cl. ..... Plt./17

[58] Field of Search ..... Plt./17

*Primary Examiner*—Robert E. Bagwill

*Attorney, Agent, or Firm*—Andrew R. Klein

[57] ABSTRACT

A Hybrid Tea rose of medium height raised as an outdoor seedling for garden decoration. It is moderately hardy according to tests conducted by All-American Rose Selections, Inc. It has more than average resistance to mildew. It has an upright-spreading growth habit and produces blooms almost continuously during the growing season. The blooms have a strong fragrance suggesting a blend of citrus and spice. Their color is coral-salmon. The flowers are borne generally on single medium-length strong stems.

1 Drawing Figure

This invention relates to a new variety of Hybrid Tea rose. The plant is a moderately hardy medium height bush seedling, raised outdoors for garden decoration. It was first propagated by Samuel McGredy, IV, in Ireland. The plant herein described was propagated in Ontario, Calif., from budwood derived from that first propagation. The description herein is based upon plants grown in Ontario, Calif.

The plant blooms freely to abundantly outdoors and almost continuously during the growing season. It holds its distinguishing characteristics through succeeding propagations by budding and bears its flowers mostly singly on strong stems of medium length. The blooms have a strong fragrance, suggesting a blend of citrus and spice. The plant appears to have a more than average resistance to mildew, at least with reference to plants grown in Southern California.

The seed parent of the new variety was "Prima Ballerina." Its pollen parent was "Ginger Rogers."

The new rose variety differs from its seed parent, Prima Ballerina, in that its flowers are generally considerably larger, usually 10–13 cm., or from 4" to 5¼", whereas the flowers on the seed parent are about 3" in diameter. The flowers of Prima Ballerina contain about 20 petals, whereas flowers of the new rose contain 27 to 36 petals with additional petaloids. The overall color effect of Prima Ballerina blooms is medium pink, whereas flowers of the new rose are coral-salmon in color.

The plant of the Prima Ballerina rose has a distinctly upright growth habit, whereas the new cultivar has an upright-spreading growth habit and actually spreads out considerably more than its seed parent.

The new cultivar differs from its pollen parent, Ginger Rogers, particularly in the following ways: Ginger Rogers has 30 petals, whereas the new rose contains 27–36 petals with additional petaloids in its flowers. The flowers of Ginger Rogers are considerably more loosely formed than flowers of the new rose.

The plant of Ginger Rogers grows very tall, whereas the plant of the new rose reaches only a medium height, for rose plants of the Hybrid Tea class.

The accompanying drawing illustrates the plant in color and shows the flowering thereof from bud to full bloom.

Throughout this specification, color names beginning with a small letter signify that the name of that color, as used in common speech, is aptly descriptive. Color names beginning with a capital letter designate values based upon the Nickerson Color Fan, put out by Munsell Color Co.

BUD

The peduncle is of average length, average to heavy caliper, erect, and with numerous fine stipitate glands. The color is near Strong Yellow Green, 5GY6/8, moderately overlaid with near Dark Red, 2.5R3/7.

Before the calyx breaks, the bud is medium in size, medium length, pointed and ovoid, with foliaceous appendages and stipitate glands on the surface of the bud and usually with foliaceous parts extending beyond the tip of the bud equal to one-half or more of its length.

As the calyx breaks, the color is between Strong Reddish Orange, 7.5R5/13, and Dark Reddish Orange, 7.5R4/11.

The inner surface of the sepals carries a fine tomentum and margins on the outer surface of the bud have stipitate glands. Margins developing under overlying sepals are lined with fine hairs.

As the first petal opens, it is from average to large in size, from medium length to long, pointed and ovoid. The color on the outside surface of the petal is between Strong Reddish Orange, 7.5R5/13, and Strong Red, 2.5R5/12. The color of the inner surface is between Strong Reddish Orange, 7.5R5/13, and Vivid Red, 5R5/13.

The bud opens up well and is not prevented from opening by cold, hot, wet or dry weather.

BLOOM

The size of the bloom when fully open is average, being from 10 cm. to 13 cm. in diameter. The petalage is double, with from 27 to 36 petals, plus 9 to 11 petaloids arranged irregularly. The bloom is cupped, full and high centered at first, becoming loosely cupped.

The petals remain at first somewhat cupped, with margins reflexed outward. Later, at maturity, the petals become more loosely cupped, with tips reflexed more gently outward.

The petals are of medium thickness, the inside being slightly velvety while the outside is slightly shiny to satiny. The outside petals are very broadly obovate; intermediate petals broadly obovate; while the inside petals are from broadly obovate to irregular. The colors may be modified by being dotted, blotched, shaded and/or washed with other colors.

The paragraphs immediately following describe color values observed in a flower newly opened in the month of September. The plant had been grown outdoors, in Ontario, Calif.

The outer surface of the outside petal is between Vivid Red, 5R5/13, and Strong Purplish Pink, 7.5RP7/10, with a very small whitish area at the point of attachment at the base. The inner surface of the outside petal is near Brilliant Yellow, 2.5Y9/9, at the base, the remainder being between Strong Reddish Orange, 7.5R5/13, and Deep Pink, 2.5R6/11.

The outer surface of the intermediate petal is between Vivid Red, 5R5/13, and Strong Purplish Red, 10RP5/12, in color, with a very small white-colored area at the point of attachment at the base. The coloration of the inner surface of the intermediate petal is the same as the inner surface of the outside petal, except that the Strong Reddish Orange, 7.5R5/13, appears more prominently.

The outer surface of the inside petal is predominately a color between Strong Red, 2.5R5/12, and Deep Pink, 2.5R6/11, with a very small whitish area at the point of attachment at the base.

The coloration of the inner surface of the inside petal is near Brilliant Yellow, 2.5Y9/9, at the base, while the remainder is near Strong Reddish Orange, 7.5R5/13.

The paragraphs immediately following describe the color values observed in a bloom which had been open for 3 days, outdoors, in the month of September. The plant had been grown outdoors, in Ontario, Calif.

The coloration of both the inside and outside petals was the same, namely, being generally between Strong Red, 2.5R5/12, and Deep Purplish Pink, 7.5RP6/12, on the outside and basically between Strong Reddish Orange, 7.5R6/12, and Deep Pink, 2.5R6/11, on the inside.

The general color effect of the newly opened flower is between Deep Yellowish Pink, 5R6/11, and Vivid Red, 5R5/13. After being three days open, the color of the bloom is near Deep Pink, 2.5R6/11. The petals drop off cleanly, except for the petaloids.

The flowers on the bush in the garden persist for 5 or more days in the month of September, in the locality named. Cut roses grown outdoors and kept at living-room temperatures will last from 3 to 5 days in the month of September.

REPRODUCTIVE ORGANS

The stamens are from average in number to many, and are arranged regularly about the pistils, a few being mixed with petaloids.

The filaments are from short to medium-length, most between 5 and 8 cm. in length. The basic color is cream, with a decided pinkish cast. Most are with anthers.

The anthers are medium in size, all opening approximately at once. Near the margins, the color is near Moderate Orange Yellow, 10YR8/10, while the remainder is a light creamy yellow color.

Pollen is somewhat sparse to moderate and near Moderate Orange Yellow, 10YR8/10, in color.

The pistils are approximately 110 in number, this being average.

The styles are uneven, of average length and caliper, and somewhat loosely bunched. The color is near Strong Red, 5R4/12.

The stigma is near Moderate Orange Yellow, 7.5YR8/8, in color.

Some of the ovaries are enclosed in the calyx, and some protrude therefrom.

Since this variety does not normally produce hips when grown outdoors in the locality named, there were no hips or seeds for description.

FOLIAGE

The compound leaves usually comprise 3 to 5 leaflets. These are normal in quantity, of medium size, and are moderately heavy, semi-glossy and slightly wrinkled. The leaflets are ovate to somewhat elliptical, with apex acute and margin doubly serrate.

The mature foliage displays upon its upper surface a coloration between Moderate Yellow Green, 2.5GY5/5, and Moderate Olive Green, 2.5GY4/3. The under surface is near, but grayer than, Brilliant Yellow Green, 7.5GY8/7.

The young foliage, on both the upper and under surface, is predominately a shade deeper than Dark Red, 2.5R3/7.

The rachis is of average size, the upper side being grooved and hairy, with some stipitate glands on the edges. The under side is sparsely prickly.

The stipules are medium-length and medium-width, with medium-length points turning out at an angle of less than 90°.

The plant has a more than average resistance to mildew when compared with other varieties now in commerce, when grown under comparable conditions at Ontario, Calif.

GROWTH

The plant is bushy and upright-spreading in habit and much to moderately branched. It displays a vigorous growth. The canes are medium to heavy in caliper.

The main stems are near Strong Yellow Green, 7.5GY6/8, in color. They carry several large prickles which are medium-length and hooked slightly downward, with medium-length moderately broad base. There are many small prickles, and both the large and small prickles are near Moderate Reddish Brown, 10R3/4, in color. There are no hairs.

The branches are near Moderate Yellow Green, 7.5GY5/7, in color. There are several large prickles which are medium-length and hooked slightly downward, with moderately narrow base. Their color is near Brownish Orange, 5YR5/8. There are a few small prickles which are the same coloration as the large prickles. There are no hairs.

New shoots are between Strong Yellow Green, 5GY6/8, and Moderate Yellow Green, 5GY5/6, in color, and strongly overlaid with near Dark Red, 2.5R3/7. There are several large prickles which are medium-length and hooked slightly downward, with medium-length moderately broad base. Their coloration is generally near Dark Red, 2.5R3/7. There are several small prickles with a coloration the same as the large prickles. There are no hairs, but several stipitate glands.

I claim:

1. An asexually reproduced rose plant of the Hybrid Tea class, substantially as herein illustrated and described, being especially characterized in a vigorous upright-spreading growth habit and a tendency to bear its blooms singly, on strong stems of medium length, said plant further being characterized in the coral-salmon color of its blooms, and the strong citrus-and-spice fragrance of the same.

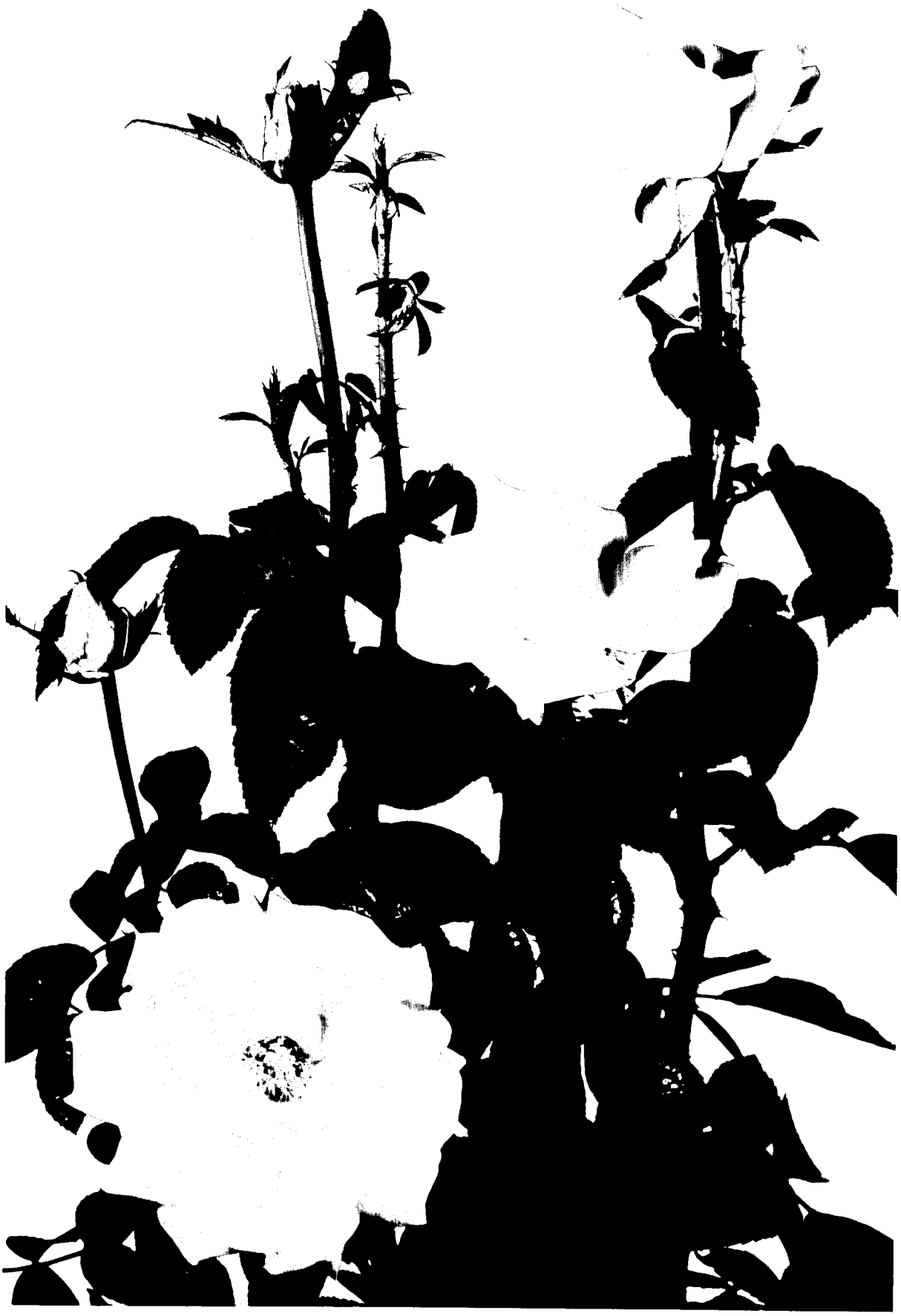

* * * * *